United States Patent [19]

McGalliard

[11] 4,152,784
[45] May 8, 1979

[54] NYLON HOSE TREATED WITH MICROENCAPSULATED HAIR DISSOLVING SOLUTION

[76] Inventor: James D. McGalliard, 11171 Fenwick Pl., Santa Ana, Calif. 92705

[21] Appl. No.: 873,814

[22] Filed: Feb. 1, 1978

[51] Int. Cl.² ............................................. A41B 11/00
[52] U.S. Cl. .......................................... 2/239; 2/409; 8/161; 128/272; 128/272.3; 128/355; 252/316
[58] Field of Search ............... 2/239, 240, 409, 243 R; 128/355, 272.3, 272 R, 260; 252/316; 8/161

[56] References Cited

U.S. PATENT DOCUMENTS

| | | | |
|---|---|---|---|
| 2,372,664 | 4/1945 | Duane | 2/239 |
| 3,470,877 | 10/1969 | Morgan | 128/355 |
| 3,565,819 | 2/1971 | Gragger | 252/316 |

*Primary Examiner*—H. Hampton Hunter
*Attorney, Agent, or Firm*—Knobbe, Martens, Olson, Hubbard & Bear

[57] ABSTRACT

A fabric garment which automatically removes unwanted hair while being worn against the skin of the user. The garment is coated with a pressure sensitive microencapsulated depilatory agent. Pressure exerted by a hair stubble against the fabric causes the microencapsulation to rupture and dispense the depilatory agent in a small localized area around the hair follicle. The depilatory agent dissolves the hair stubble without irritating the user's skin.

17 Claims, 3 Drawing Figures

U.S. Patent May 8, 1979 4,152,784
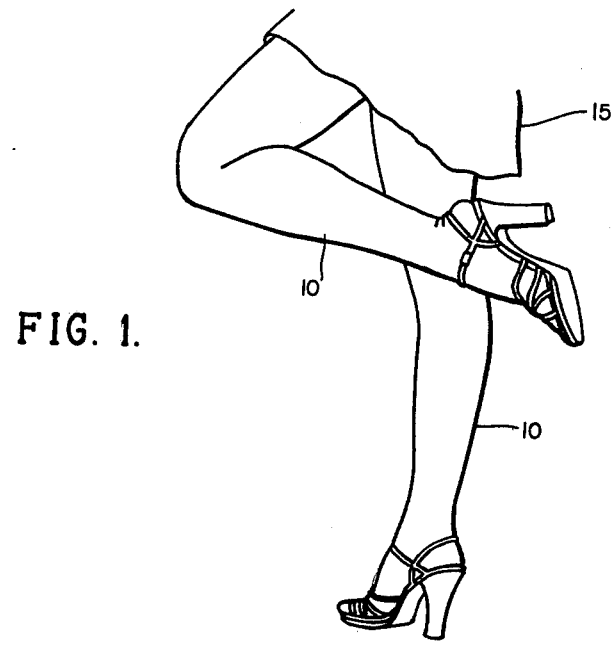
FIG. 1.
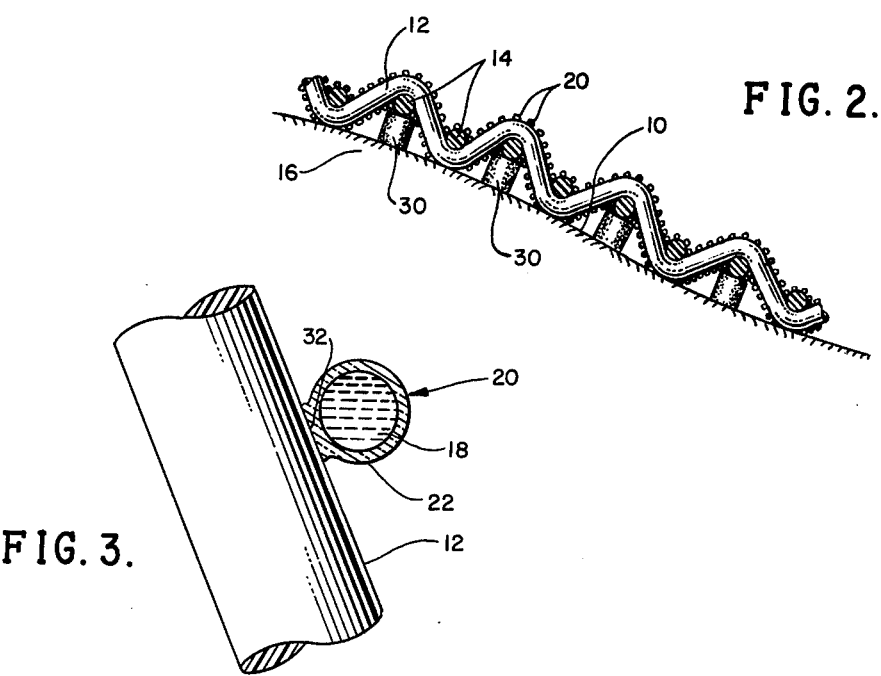
FIG. 2.
FIG. 3.

NYLON HOSE TREATED WITH MICROENCAPSULATED HAIR DISSOLVING SOLUTION

BACKGROUND OF THE INVENTION

This invention relates to a fabric garment to be worn tightly against the skin of a user, which during use, automatically removes unwanted hair. More particularly, the invention relates to hosiery which is coated with a microencapsulated depilatory agent which automatically dispenses the depilatory to only a localized area around the hair follicle thereby dissolving the hair without irritating the user's skin.

Throughout the ages, man has developed various devices and methods for removing unwanted body hair. These prior art devices have ranged from mechanical cutting edges which shave the hair stubble adjacent to the skin such as straight, safety, and electric razors, to modern depilatory agents which are applied directly to the skin to dissolve the hair stubble by a chemical process. Although these methods and devices have proven useful in many applications, there are inherent deficiencies in their use.

Since the cutting edge devices contact the hair stubble as they are pulled across the skin of the user, there is a tendency for the hair to bend, causing a failure to shave the hair close to the skin. Additionally, these mechanical devices suffer from the all too frequent cutting of the user's skin as well as the hair stubble.

Alternatively, the depilatory agents, although capable of chemically dissolving the hair close to the skin, in many instances cause minor skin irritation to the user or possess an obnoxious sulfide odor which is extremely difficult to mask.

Further, a major limitation of both the mechanical edge devices and depilatory agents are that they are time-consuming to use. When using cutting edge devices, pre-shave lotions or lather must first be applied to the skin to soften the hair stubbles and protect the skin from abrasion. Then, subsequent to shaving, these lotions must be rinsed from the skin with water. Similarly, use of the depilatory agents require that a hair dissolving lotion be applied and left in contact with the skin for a period of time and then be removed by washing. In many instances, use of these prior art devices and methods require as much as thirty minutes be expended each day by the user in removing unwanted body hair.

SUMMARY OF THE INVENTION

The applicant has discovered a convenient and economical device and method for automatically removing unwanted body hair which substantially eliminates these deficiencies of the prior art.

The present invention provides a garment which is coated with a microencapsulated depilatory agent which effectively and automatically removes unwanted body hair when worn by the user. The invention is extremely suitable for use in womens' hosiery which is typically worn tightly against the skin of the user.

The invention comprises hosiery which is coated with a pressure sensitive microencapsulated depilatory agent. This microencapsulation facilitates deposition of the liquid depilatory upon the hosiery in a capsule form without wetting or altering the original dry appearance of the fabric, and additionally allows the dispensing of the depilatory to only a localized area adjacent the hair stubble.

When the hosiery of the present invention is worn tightly over the skin of the user, the pressure exerted by the hair stubble against the fabric ruptures the microencapsulation, thereby selectively releasing the depilatory agent in the area surrounding the hair stubble. The depilatory agent quickly begins to break down the protein structure of the hair and completely dissolves the hair stubble during normal wearing of the garment.

As can be readily seen, the present invention alleviates the time consumption deficiencies of the prior art by providing hosiery which automatically removes unwanted hair while being worn. Additionally, the present invention automatically removes hair close to the skin surface without the possibility of accidental cutting of the skin. Further, due to the localized area of contact between the depilatory and the hair, contact between the depilatory and the user's skin is minimized. This permits prolonged contact duration of the depilatory with the hair stubble, so that a moderate strength depilatory agent can be used which does not possess an unpleasant odor. The microencapsulation, by limiting skin contact with the depilatory (only the hair stubble ruptures the capsules), permits the use of depilatory chemicals which would be too harsh to apply directly to the skin for prolonged periods.

These and other features of the present invention will become more apparent upon reference to the drawings wherein:

FIG. 1 is a schematic view of a nylon hose coated with a microencapsulated depilatory and being worn tightly against the skin of the user;

FIG. 2 is an enlarged pictorial representation of the nylon hose against the skin of the user showing the spacial relationship between the fabric, hair stubble and the microencapsulated depilatory; and FIG. 3 is an enlarged cross-sectional view showing a filament of the nylon hose with a microencapsulated depilatory thereon.

DETAILED DESCRIPTION OF THE PREFERRED EMBODIMENT

Referring to FIG. 1, there is shown the microencapsulated depilatory coated hosiery 10 of the present invention being worn around the legs of a user 15. As can be seen, it is advantageous if the fabric, in this case the hosiery 10, is capable of being tightly worn in direct contact with the user's skin 15, yet be elastic enough to stretch and conform to normal body movement.

The hosiery 10 is preferably formed of a looped fabric knit and made from synthetic fibers such as nylon or rayon which are typically used in hosiery manufacturing. Such looped fabric construction is well known in the art and provides hosiery having high elastic and memory properties which easily stretch to accommodate body movement and quickly return to the pre-stretched configuration of the fabric after such movement. Additionally, the synthetic fibers possess high strength and are easily dyed to allow the hosiery to be manufactured in a variety of cosmetically pleasing colors.

The microencapsulation process utilized in the present invention is a relatively new technology which has been significantly developed in recent years. Basically, this microencapsulation process comprises the formation of a hard thin shell or film which coats a minute-sized liquid depilatory material, thereby forming a pressure sensitive depilatory capsule. Various microencapsulation processes suitable for use in the present invention are well known in the art and are disclosed in U.S. Pat. No. 3,804,775 (gelatin phase change), U.S. Pat. No. 3,607,775 (complex coacervation), U.S. Pat. No. 2,800,458 (salt coacervation), and U.S. Pat. No. 3,565,819 (wax-hydrophilic colloid), the descriptions thereof incorporated herein by reference.

These pressure-sensitive depilatory capsules 20 are schematically shown in FIG. 3, and include a depilatory, liquid core 18 and a surrounding, typically spherical wall 22. The capsules 20 typically range from a few to several hundred microns in diameter, and are deposited upon the hosiery 10, thereby contacting the hair stubble 30 as well as the user's skin 16 during use.

The dispersion of depilatory capsules 20 is preferably sprayed or coated upon the hosiery 10 immediately after the microencapsulation process is accomplished. At this stage in the process, the outer walls of each capsule are wetted and substantially pliable. This wetted, soft condition allows each capsule to adhere and conform to the shape of the hosiery fabric. Referring to FIG. 3, it can be seen that at the interface of the microcapsule 20 and the hose filament 12, the generally spherical shaped wall 22 of the microcapsule deforms into a substantially flat surface 32 which effectively bonds the microcapsule 20 to the hosiery 10. Subsequently, the hosiery 10 with the dispersion of capsules 20 thereon in dried at an elevated temperature and the capsule walls hardened around the fabric, thereby adhering each capsule to the hosiery 10. Alternatively, depositing of the capsules 20 may be accomplished by initially drying the capsules to form a powder-like substance and then spraying the capsules upon the hosiery 10 with a moderate, water insoluble adhesive.

The liquid depilatory agent is contained within the microcapsules 20 must be inert to the microcapsule wall material, and still reduce the disulfide cross-links of body hair, preferably without causing substantial irrigation to the user's skin. Solutions having a moderate concentration of calcium thioglycolate or 1,4 dimercapto-2,3 butane diol have been found to be preferable over sulfate or sulhydrate solutions due to their non-obnoxious odor and non-skin irritant properties. Such calcium thioglycolate and dimercapto butane diol depilatories are disclosed in U.S. Pat. No. 3,527,559 and U.S. Pat. No. 3,865,546, respectively, which are incorporated herein by reference.

The automatic hair removing process of the present invention can now be described. Referring to FIG. 2, it can be seen that the hosiery 10 is composed of lengthwise and cross-wise extending nylon filaments 12 and 14, respectively, which form a looped fabric knit. Depending upon the desired sheerness, these filaments typically measure 0.003 to 0.012 of an inch in diameter.

The hosiery 10 is coated with a dispersion of microcapsules 20. A hair stubble 30 which initiates from a hair follicle (not shown) extends outward from the skin surface 16.

In use, the hosiery 10 is tightly worn over the user's skin 16 and is in direct contact with the hair stubble 30. Due to the outward protrusion of the hair stuble 30, increased pressure in the area adjacent the hair stubble 30 is exerted upon the outer walls 22 of the depilatory microcapsules 20. This pressure causes the walls 22 to rupture, thereby releasing the depilatory 18 in a localized area at the hair stubble 30. Upon contact with the hair stubble 30, the depilatory 18 immediately begins to reduce the disulfur cross-links of the hair and completely dissolves the stubble 30 within the normal course of wearing, for example, a day.

It is advantageous to select a microencapsulation material and thickness which ruptures in response to either abrasion by the hair stubble, or the increased pressure at the stubble but which will not ordinarily rupture when pressed against the user's skin.

As can be easily recognized, due to the hosiery being typically worn throughout the day, the hair removal process can extend over a period of hours, thereby allowing the use of a more moderate strength depilatory which is less irritating to the user's skin. Additionally, since the depilatory is only released in a localized area at the hair stubble, rather than over the entire leg area, these skin irritation effects are further reduced.

In the preferred embodiment, the hosiery is designed for single usage and is easily disposed of after wearing. However, with careful handwashing and air drying, multiple usage of the hosiery may be accomplished.

What is claimed is:

1. A garment wearable by a person to automatically remove unwanted hair, comprising:
   fabric coated with plural microcapsules;
   a liquid depilatory agent contained within said plural microcapsules; and
   said microcapsules comprising a pressure-sensitive thin shell which releases said depilatory agent in response to pressure exerted by a hair stubble, said depilatory reducing the disulfur cross-links of said hair stubble upon contact therewith.

2. The garment of claim 1 wherein said thin shell selectively releases said depilatory agent at said hair stubble.

3. The garment of claim 1 wherein said depilatory agent chemically removes said hair stubble without irritating the skin of the user.

4. The garment of claim 1 wherein said depilatory agent is inert with respect to said thin shell.

5. A device for removing hair stubble from legs comprising:
   a stocking worn against the skin of a user;
   minute, easily frangible capsulation means on the fabric of said stocking, said means being rupturable by the pressure of said hair stubble thereagainst; and
   a liquid depilatory contained within said capsulation means, said depilatory being released upon rupture of said capsulation means to chemically remove said hair stubble.

6. The device of claim 5 wherein said stocking comprises a snug-fitting hosiery.

7. The device of claim 5 wherein said depilatory agent comprises a non-skin irritating liquid solution.

8. The device of claim 5 wherein said depilatory is inert with respect to said capsulation means.

9. A device for automatically removing hair from legs comprising:
   a hosiery worn tightly against the skin of a user; and
   a dispersion of pressure-sensitive depilatory capsules carried by said hosiery, said capsules rupturing and releasing a fluid depilatory agent in a localized area surrounding a hair stubble upon pressure exerted by said hair stubble against said capsules.

10. The process of coating hosiery with a liquid depilatory agent comprising the steps of:
    encapsulating said liquid depilatory agent in easily frangible, hard shelled microcapsules; and depositing a large plurality of said microcapsules upon surfaces of hosiery.

11. The process of removing body hair comprising the steps of:
microencapsulating a liquid depilatory agent in plural, thin-walled, pressure-sensitive shells;
depositing said microencapsulated depilatory agent upon a flexible substrate;
contacting said substrate against the hair stubbled skin of a user; and
rupturing said thin shell by pressure exerted by a hair stubble on said shell to selectively release said liquid depilatory agent in a localized area surrounding said hair stubble, said depilatory agent chemically removing said hair stubble upon contact therewith.

12. A device to remove body hair comprising:
a flexible material coated with plural microcapsules; and
liquid depilatory agent contained within said plural microcapsules, said microcapsules comprising a micro-thin shell which selectively releases said depilatory agent for contacting a hair stubble in response to pressure exerted by said hair stubble when said flexible material tightly contacts the skin of a user.

13. A device for automatically removing body hair comprising:
a flexible material having a depilatory agent contained thereon; and
means responsive to the presence of a hair stubble extending above said body for automatically dispensing said depilatory agent in a localized area at said hair stubble when said flexible material is held against said body of a user to remove said hair stubble while limiting the application of said agent to said body itself.

14. The device of claim 13 wherein said means for dispensing said depilatory agent comprises a plurality of microcapsules storing said depilatory agent and having pressure-sensitive thin shells which release said depilatory agent in response to pressure exerted by said hair stubble.

15. The process of removing body hair comprising:
depositing a depilatory agent on a flexible material to be held against the skin of a user; and
automatically releasing said depilatory agent from said flexible material in a localized area at a hair stubble in response to the presence of said hair stubble extending beyond said skin.

16. The process of claim 15 wherein said step of depositing said depilatory agent includes microencapsulating said agent in plural, thin-walled pressure-sensitive shells; and
bonding said microcapsule shells to a surface of said flexible material.

17. The process of claim 16 wherein said releasing step comprises the rupturing of said thin-walled pressure-sensitive shells by pressure exerted on said shells by said hair stubble.

* * * * *